United States Patent [19]
Krishnamurthy

[11] Patent Number: 5,318,884
[45] Date of Patent: Jun. 7, 1994

[54] PHOTOGRAPHIC SILVER HALIDE MATERIAL CONTAINING A COUPLER HAVING A COUPLING-OFF GROUP COMPRISING A CARBOCYCLIC OR HETEROCYCLIC RING HAVING A SILYL SUBSTITUENT DIRECTLY ATTACHED THERETO

[75] Inventor: Sundaram Krishnamurthy, Penfield, N.Y.

[73] Assignee: Eastman Kodak Company, Rochester, N.Y.

[21] Appl. No.: 986,841

[22] Filed: Dec. 7, 1992

[51] Int. Cl.$^5$ ............................................... G03C 1/46
[52] U.S. Cl. .................................... 430/503; 430/385; 430/387; 430/389; 430/543; 430/553; 430/555; 430/557; 430/558; 430/955
[58] Field of Search ............... 430/503, 376, 385, 389, 430/387, 957, 553, 555, 557, 558, 543, 955

[56] References Cited

U.S. PATENT DOCUMENTS

| | | | |
|---|---|---|---|
| 3,935,015 | 1/1976 | Arai et al. | 96/74 |
| 4,483,918 | 11/1984 | Sakai et al. | 430/372 |
| 4,853,319 | 8/1989 | Krishnamurthy et al. | 430/387 |
| 4,973,545 | 11/1990 | Moore | 430/376 |

*Primary Examiner*—Charles L. Bowers, Jr.
*Assistant Examiner*—Geraldine Letscher
*Attorney, Agent, or Firm*—Arthur E. Kluegel

[57] ABSTRACT

Photographic silver halide materials and processes employ at least one coupler having a coupling-off group which includes a carbocyclic or heterocyclic ring which bears a silyl substituent on at least one of its ring carbon atoms and is attached via another of its ring atoms either directly or through a linking group or atom to the coupling position of the coupler. The silyl substituent bears three groups which are independently aromatic groups, heterocyclic groups, aliphatic groups or additional silyl groups bonded through a linking atom to the silicon atom in said silyl substituent.

14 Claims, No Drawings

PHOTOGRAPHIC SILVER HALIDE MATERIAL CONTAINING A COUPLER HAVING A COUPLING-OFF GROUP COMPRISING A CARBOCYCLIC OR HETEROCYCLIC RING HAVING A SILYL SUBSTITUENT DIRECTLY ATTACHED THERETO

BACKGROUND OF THE INVENTION

This invention relates to photographic compounds, such as couplers, that comprise a novel group capable of being released during photographic processing, and to photographic materials and processes using such compounds.

Images are commonly obtained in the photographic art by a coupling reaction between the development product of a silver halide color developing agent, particularly an oxidized aromatic primary amino developing agent, and a color forming compound commonly described as a coupler. The dyes formed vary depending upon the composition of the coupler and the developing agent. The subtractive process of color formation is typically employed in multicolor photographic elements Resulting dyes are typically cyan, magenta and yellow dyes formed in or adjacent to silver halide layers sensitive to radiation complementary to the radiation absorbed by the image dyes, that is, silver halide emulsions sensitive to red, green and blue radiation.

Compounds that release a group, particularly couplers that release a coupling-off group, are known in photographic materials, such as those described in U.S. Pat. No. 3,935,015; 4,483,918; and 4,853,319. Such compounds often do not have the desired degree of stability in such photographic materials, particularly during storage before exposure. It is important to choose coupling-off groups which provide the desired increase in coupling reactivity, but which do not cause undesired losses in sensitometric effects or in the stability of the resulting image dyes There has been a need for a new class of compounds, particularly dye-forming couplers, that comprises a group that is capable of being released upon processing in a photographic silver halide material such that the coupler has a higher activity (gamma) and the dye image obtained on color processing has increased resistance to changes caused by heat, light and humidity.

SUMMARY OF THE INVENTION

These needs have been satisfied by providing a coupler having a coupling-off group which comprises a carbocyclic or heterocyclic ring which bears a silyl substituent on at least one of its ring carbon atoms and is attached via another of its ring atoms either directly or through a linking group or atom to the coupling position of said coupler, wherein said silyl substituent bears three groups which are independently aromatic groups, heterocyclic groups, aliphatic groups, or additional silyl groups, said silyl groups being bonded through a linking atom to the silicon atom in said silyl substituent.

There are also provided photographic elements and emulsions comprising photographic couplers according to the invention, and processes for developing an image in a photographic element using said photographic couplers.

DETAILED DESCRIPTION OF THE INVENTION

Related couplers and processes for synthesis thereof are disclosed in dockets no. 56852 and 62911 which are equivalent to U.S. Ser. Nos. 07/987,047 and 07/986,240 respectfully which were each filed on Dec. 7, 1992, filed simultaneously, which are incorporated in the entireties herein by reference.

In a preferred embodiment of the invention, the photographic coupler is represented by the formula:

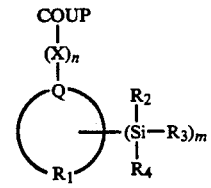

wherein
COUP is a coupler moiety;
m is 1, 2 or 3;
X is O, S, or a linking group;
n is 0 or 1;
Q is a carbon atom or nitrogen atom, with the proviso that when Q is carbon, n is i and X is O, S or amino, and when Q is nitrogen, n is 0 or 1 and X is $OC(R)_2$;
R is hydrogen, $C_{1-30}$ alkyl or $C_{6-30}$ aryl;
$R_1$ represents the atoms necessary to complete an unsubstituted or substituted carbocyclic or heterocyclic ring; and
$R_2$, $R_3$ and $R_4$ individually are unsubstituted or substituted groups that are hydrolytically stable and compatible with COUP.

The term COUP herein means a coupler moiety as used in the photographic art. The coupler moiety can be any moiety that will react with an oxidized color developing agent to release the described coupling-off group. It includes coupler moieties that form colored products on reaction with oxidized color developing agents, for example, any cyan, magenta or yellow dye-forming coupler moiety, and coupler moieties that form colorless products on such a reaction. Preferred COUP moieties are pyrazolone coupler moieties.

Representative couplers which form cyan dyes upon reaction with oxidized color developing agent are described in the following patents and publications: U.S. Pat. Nos. 2,367,531; 2,423,730; 2,474,293; 2,772,162; 2,801,171; 2,895,826; 3,002,836; 3,034,892; 3,041,236; 3,419,390; 3,476,563; 3,772,002; 3,779,763; 3,996,253; 4,124,396; 4,254,212; 4,296,200; 4,333,999; 4,443,536; 4,457,559; 4,500,635; 4,526,864; 4,690,889; 4,775,616; and in "Farbkuppler—ein Literaturübersicht," published in Agfa Mitteilungen, Band III, pp. 156–175 (1961). Preferred couplers are phenols and naphthols. Exemplary coupler moieties include:

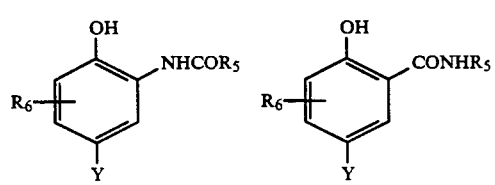

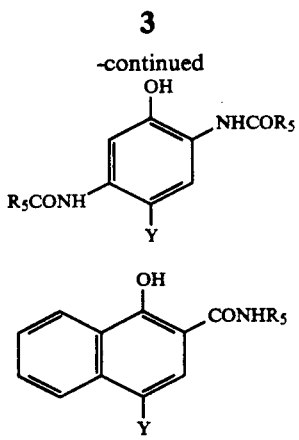

where $R_5$ represents a ballast group, and $R_6$ represents halogen, $C_{1-4}$ alkyl, or $C_{1-4}$ alkoxy. Preferred $R_6$ groups include Cl, F, methyl, ethyl, butyl, methoxy, ethoxy and butoxy.

Representative couplers that form magenta dyes upon reaction with oxidized color developing agent are described in U.S. Pat. Nos. 1,269,479; 2,311,082; 2,343,703; 2,369,489; 2,600,788; 2,673,801; 2,908,573; 3,061,432; 3,062,653; 3,152,896; 3,519,429; 3,725,067; 3,935,015; 4,120,723; 4,443,536; 4,500,630; 4,540,654; 4,581,326; 4,774,172; European Patent Applications 170,164; 177,765; 284,239; 284,240; and in "Farbkuppler—ein Literaturübersicht," published in Agfa Mitteilungen, Band III, pp. 126–156 (1961). Preferred couplers are pyrazolones, pyrazolotriazoles and pyrazolobenzimidazoles. Exemplary couplers moieties the following:

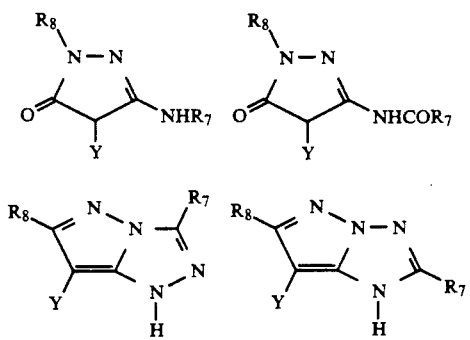

wherein $R_7$ and $R_8$ are independently a ballast group, unsubstituted or substituted alkyl, phenyl or substituted phenyl.

Typical couplers which form yellow dyes upon reaction with oxidized color developing agents are described in

| U.S. Pat. Nos. | | | |
|---|---|---|---|
| 3,048,194; | 2,298,443; | 2,407,210; | 2,875,057; |
| 3,447,928; | 3,265,506; | 3,384,657; | 3,415,652; |
| 4,022,620; | 3,542,840; | 3,894,875; | 3,933,501; |
| 4,203,768; | 4,046,575; | 4,095,983; | 4,182,630; |
| 4,443,536; | 4,221,860; | 4,326,024; | 4,401,752; |
| 4,617,256; | 4,529,691; | 4,587,205; | 4,587,207; |

European Patent Application 296,793; and in "Farbkuppler—ein Literaturübersicht," published in Agfa Mitteilungen, Band III, pp. 112–126 (1961). Preferred yellow dye forming couplers are acylacetanilides such as benzoylacetanilides and pivalylacetanilides. Exemplary coupler moieties include the following:

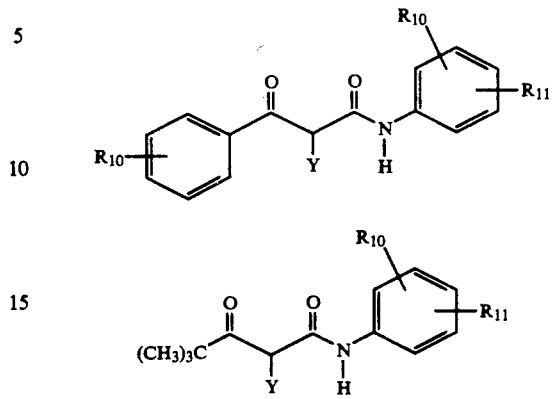

wherein $R_9$ is a ballast group, unsubstituted or substituted alkyl, phenyl or substituted phenyl as described above, and $R_{10}$ and $R_{11}$ are independently hydrogen, halogen, $C_{1-4}$ alkyl, or a ballast group such as $C_{16-20}$ alkoxy.

Couplers which form colorless products upon reaction with an oxidized color developing agent are described in U.K. Pat. No. 861,138; U.S. Pat. Nos. 3,632,345; 3,928,041; 3,958,993; and 3,961,959. Preferably, such couplers are cyclic carbonyl-containing compounds that have the coupling-off group attached to the carbon atom in the α-position with respect to the carbonyl group. Structures of preferred colorless coupler moieties include the following:

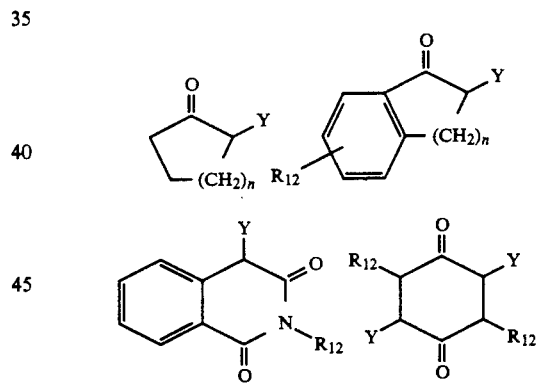

wherein $R_{12}$ is a ballast group, unsubstituted or substituted alkyl, phenyl or substituted phenyl as described above, and n is 1 or 2.

Couplers which form black dyes upon reaction with oxidized color developing agents are described, for example, in U.S. Pat. Nos. 1,939,231; 2,181,944; 2,333,106; and 4,126,461; German OLS No. 2,644,194 and 2,650,764. preferred couplers are resorcinols or m-aminophenols having the coupling-off group para to a hydroxyl group. Structures of preferred coupler moieties include the following:

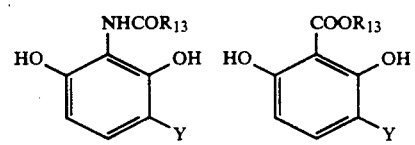

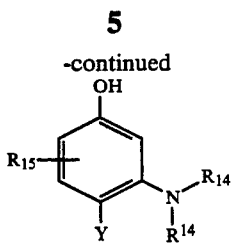

wherein $R_{13}$ is $C_{3-20}$ alkyl, phenyl, which can be substituted with hydroxy, halo, amino, $C_{1-20}$ alkyl or $C_{1-20}$ alkoxy, each $R_{14}$ is independently hydrogen, $C_{1-20}$ alkyl, $C_{2-20}$ alkenyl, or $C_{6-20}$ aryl, and $R_{15}$ is halogen, $C_{1-20}$ alkyl, $C_{1-20}$ alkoxy or a similar monovalent organic group.

Additional coupler moieties to which the above-described coupling-off group can be attached are described, for example, in U.S. Pat. No. 4,248,962 and WO 88/04795.

The X as described is an oxygen atom, sulfur atom, amino group, or a linking group that is bonded to the coupler moiety at a coupling position. The X enables the coupling-off group to be released upon processing of the photographic element containing the coupler. An illustrative linking group is

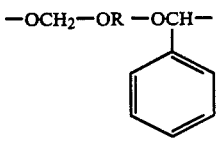

$R_1$ represents atoms, preferably carbon, nitrogen and/or oxygen atoms, that complete a ring, preferably a 5- or 6-membered ring, with Q, and that can be substituted with the described silyl substituent. Exemplary rings include pyridine, pyrazole, pyrrole and triazole, and preferably benzene. The ring completed by $R_1$ can be substituted with only the silyl group as described, or it can bear further substituents such as halogen or alkyl groups that do not adversely affect the coupler or photographic element of the invention.

$R_2$, $R_3$ and $R_4$ can be any groups that are unsubstituted or substituted and do not adversely affect the coupler or the photographic element of the invention. These groups can be, for example, unsubstituted or substituted alkyl, alkenyl, cycloalkyl, aryl, heterocyclic, silyloxy or aryloxy groups. Exemplary groups include unsubstituted or substituted $C_{1-30}$ alkyl groups; $C_{2-30}$ alkenyl groups such as allyl and vinyl; $C_{6-30}$ cycloalkyl; $C_{6-30}$ aryl: heterocyclic; silyloxy, such as trimethylsilyloxy, phenyldimethylsilyloxy, and t-butyldimethylsilyloxy; $C_{1-30}$ alkoxy; and $C_{6-30}$ aryloxy groups. $C_{1-30}$ alkyl groups, allyl and vinyl groups, and the foregoing silyloxy groups are especially preferred.

Particularly useful couplers as described comprise a coupling-off group that is a trialkylsilylarylthio group, particularly an o-trialkylsilylphenylthio group represented by the structure:

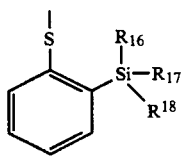

wherein $R_{16}$, $R_{17}$; and $R_{18}$ are individually alkyl groups, as described.

The described groups in the silyl group, particularly the alkyl groups in the trialkylsilyl group, can be unsubstituted or optionally substituted with groups that do not adversely affect the desired properties of the couplers or the dye formed. The alkyl group can, for example, contain from 1 to 30 carbon atoms. Exemplary alkyl groups include methyl, ethyl, propyl, n-butyl, t-butyl, pentyl, octyl, eicosyl, and triacontyl. The alkyl group can be optionally substituted with, for example, halogen (such as Cl, Br or F), hydroxy, carboxy, alkoxy, sulfonamido, sulfamyl, amino, carbonamido, sulfonyl, aryloxy, alkyl, and aryl (such as phenyl and naphthyl), or phenolic, carbocyclic or heterocyclic groups.

The described aryl and heterocyclic groups can also be unsubstituted or optionally substituted with groups that do not adversely affect the desired properties of the couplers or dyes formed from the couplers. The aryl group can contain, for example, 6 to 30 carbon atoms. Phenyl and naphthyl groups are illustrative aryl groups. The substituents can be, for example, halogen (such as Cl, Br and F); $C_{1-30}$ alkyl such as methyl, ethyl, propyl, n-butyl, t-butyl, pentyl, octyl, eicosyl, or triacontyl; hydroxy, carboxy, nitro, alkoxy, sulfonamido, sulfamyl, carbonamido, sulfonyl, aryloxy, alkyl, aryl, carboxylic esters, and heterocyclic groups.

Substituents on the described couplers can include ballast groups that are known to be useful in the photographic art. In addition, the couplers can be monomeric, oligomeric or polymeric (i.e., "substituents" can include additional coupler moieties).

The coupler moiety can be unballasted or ballasted. In other words, the coupler moiety can optionally include a group of such molecular size and configuration as to render the coupler nondiffusible from the layer in which it is coated in a photographic element. Ballast groups are described, for example, in U.S. Pat. Nos. 4,420,556 and 4,923,789. Couplers as described can be attached to ballast groups or to polymeric chains through one or more of the groups of the coupler moiety or through the coupling-off group. For example, one or more of the couplers can be attached to the same ballast group. Representative ballast groups include unsubstituted or substituted alkyl or aryl groups containing 8 to 32 carbon atoms. Representative ballast groups include ethers, thioethers, sulfones as well as carboxylic, sulfonic and phosphoric esters and amides containing unsubstituted or substituted alkyl or aryl groups comprising about 8 to 32 carbon atoms. Representative substituents on these alkyl and aryl groups include alkyl, aryl, alkoxy, aryloxy, alkylthio, arylthio, hydroxy, halogen, alkoxycarbonyl, aryloxycarbonyl, carboxy, acyl, acyloxy, amino, anilino, carbonamido, carbamoyl, alkanesulfonyl, arenesulfonyl, sulfonamido and sulfamyl groups. The alkyl portion of these substituents can contain, for example, i to 30 carbon atoms. The aryl portion of these substituents can contain, for example, 6 to 30 carbon atoms.

The coupler moiety can be monomeric, or it can form part of a dimeric, oligomeric or polymeric coupler.

The couplers as described can be used in ways and for purposes that dye-forming couplers have been used in the photographic art.

Examples of such couplers include:

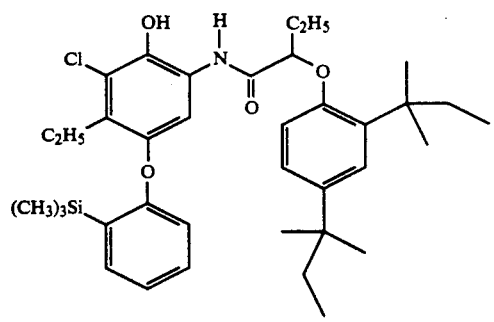
(1)
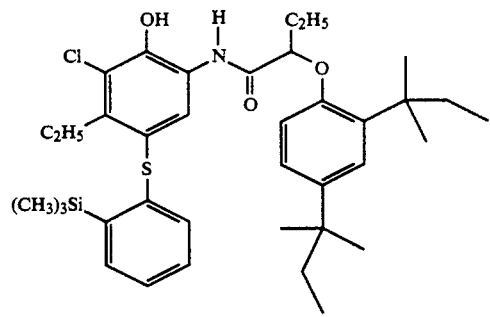
(2)
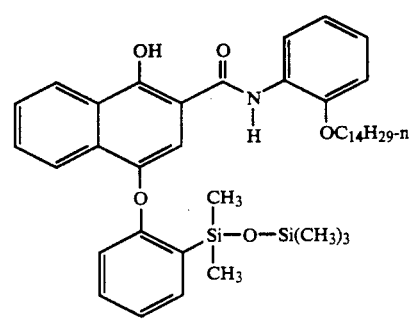
(3)
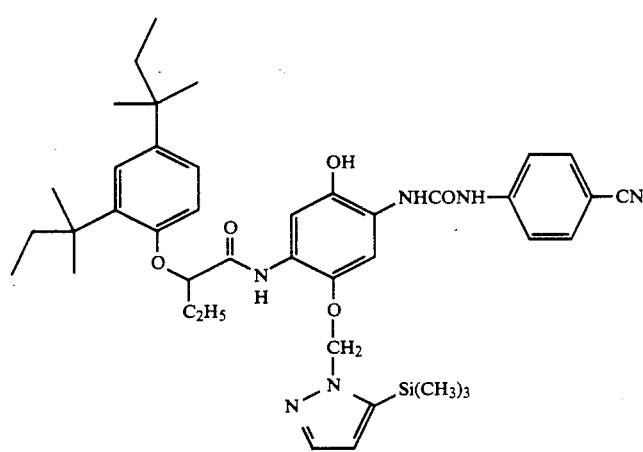
(4)
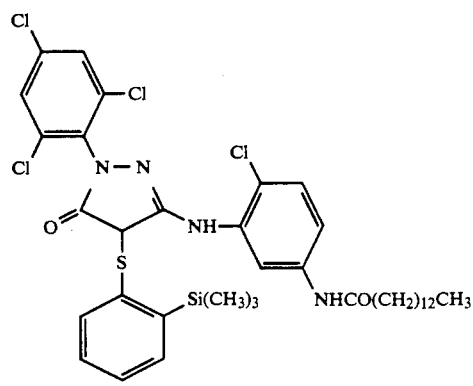
(5)

-continued
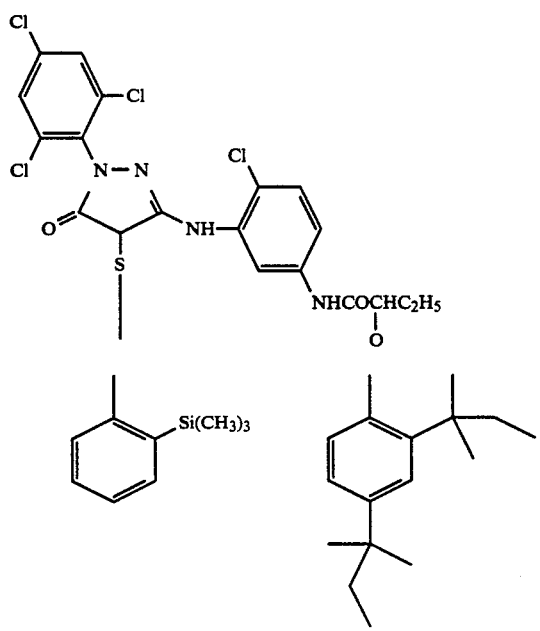
(6)
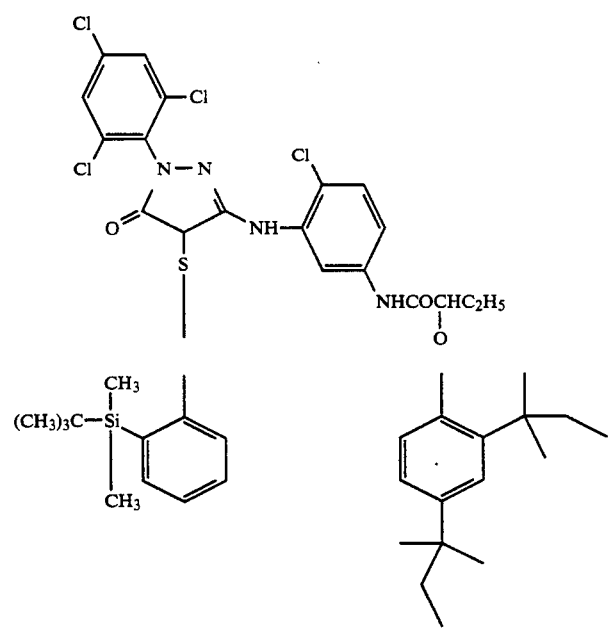
(7)
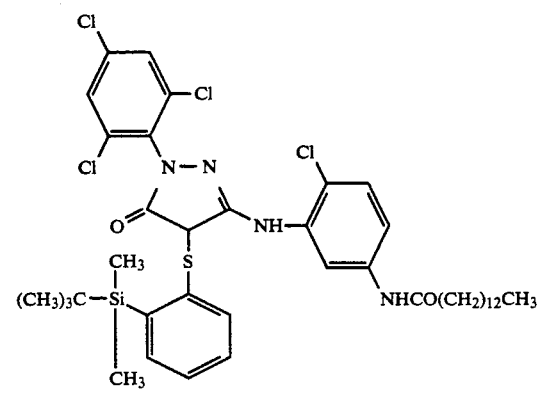
(8)

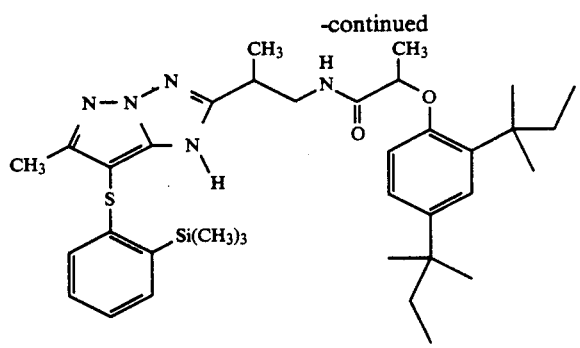

(9)

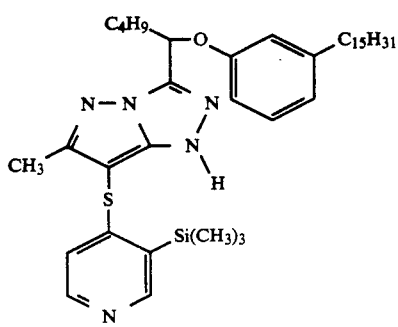

(10)

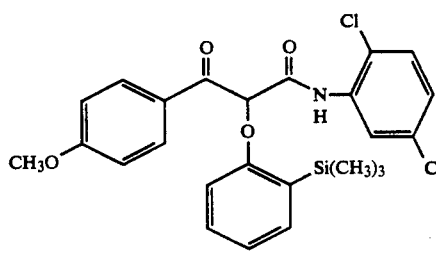

(11)

(12)

The photographic couplers according to the invention can be prepared by simplified methods of preparation known in the organic synthesis art. For example, an o- or m-silyl substituted aromatic or heterocyclic thiophenol or phenol can be prepared, without isolation of intermediates, as follows. O- or m-bromo aromatic or heterocyclic thiol or phenol is reacted with excess disilazane, particularly hexaalkyldisilazane in the presence of an imidazole catalyst at a temperature within the range of about 60° to 150° C., preferably 60° to 100° C., until reaction completion, such as within about 1 to 3 hours. Next, an organic solvent such as ether, that is compatible with n-butyllithium, is added, typically to provide about a 0.5 to 1.5 molar mixture. The resulting reaction mixture is cooled to below 0° C., preferably to within the range of about −5° C. to −10° C. Then a metallizing reagent, preferably n-butyllithium, in an organic solvent, such as hexane, is added dropwise at a 1 equivalent concentration, to form a metallized intermediate. The resulting reactants are mixed until reaction (rearrangement) completion, but before formation of significant S- or O-alkylated by-products. Finally, the reaction is quenched, preferably by addition of acid, such as hydrochloric acid.

When the corresponding hexaalkyldisilazane is not readily available, the S-trialkylsilylarylthiol or phenol intermediate can readily be synthesized from the corresponding trialkylsilyl chloride and the 2-bromothiophenol or 2-bromophenol in the presence of an organic base, such as triethylamine, or an inorganic base, such as sodium hydride, under anhydrous conditions.

The resulting intermediate can be then reacted with a parent photographic coupler moiety to form a photographic coupler according to the invention by methods known in the organic compound synthesis art.

The inventive couplers can be used alone, or in combination with other couplers known in the photographic art.

Typically, the couplers are associated with at least one silver halide emulsion layer coated on a support to form a photographic element. As used herein, the term "associated herewith" signifies that the coupler is incorporated in the silver halide emulsion layer or in a layer adjacent thereto where, during processing, it is capable of reacting with the silver halide development products.

Typically the coupler is dissolved in a coupler solvent, and the solution is dispersed in an aqueous gelatin solution. Examples of coupler solvents that can be used are dibutyl phthalate, tricresyl phosphate, diethyl lauramide and 2,4-di-tert-amylphenol. In addition, an auxiliary coupler solvent known in the photographic art can be used.

The photographic elements according to the invention can be single color elements or multicolor elements. In a multicolor element, the dye-forming couplers as described can be associated with any of the emulsion layers or dye-forming units. If the coupler is a pyrazolone coupler, it is typically associated with a green-sensitive emulsion. The couplers can be associated with an emulsion layer sensitized to a region of the spectrum complementary to the dye formed by the coupler upon processing, although they can be associated with an emulsion sensitized to a different region of the spectrum or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders known in the art.

A typical multicolor photographic element comprises a support bearing a cyan dye image-forming unit comprised of at least one red-sensitive silver halide emulsion layer having associated therewith at least one cyan dye-forming coupler; a magenta dye image-forming unit comprised of at least one green-sensitive silver halide emulsion layer having associated therewith at least one magenta dye-forming coupler; and a yellow dye image-forming unit comprised of at least one blue-sensitive silver halide emulsion layer having associated therewith at least one yellow dye-forming coupler. The element can contain additional layers, such as filter layers. At least one of the layers of the element has a coupler of the invention associated with it.

In the following discussion of suitable materials for use in the emulsions and elements of the invention, reference will be made to Research Disclosure, December 1989, Item 308119, published by Kenneth Mason Publications, Dudley Annex, 21a North Street, Emsworth, Hampshire P010 7DQ, England. This publication will be identified hereinafter as "Research Disclosure".

The silver halide emulsion employed in the elements as described can be either negative-working or positive-working. Suitable emulsions and their preparation are described in Research Disclosure Section I and II and the publications cited therein. Suitable vehicles for the emulsion layers and other layers of elements of the invention are described in Research Disclosure Section IX and the publications cited therein.

In addition to the couplers described above, the element of the invention can include added couplers as described in Research Disclosure Section VII, paragraphs D, E, F, and G and the publications cited therein. These couplers can be incorporated in the elements and emulsions as described in Research Disclosure Section VII, paragraph C and the publications cited therein.

The photographic elements of the invention or individual layers thereof can contain brighteners (see Research Disclosure Section V), antifoggants and stabilizers (see Research Disclosure Section VI), antistain agents and image dye stabilizers (see Research Disclosure Section VII, paragraphs I and J), light absorbing and scattering materials (see Research Disclosure Section VIII), hardeners (see Research Disclosure Section X), coating aids (see Research Disclosure Section XI), plasticizers and lubricants (see Research Disclosure Section XII), matting agents (see Research Disclosure Section XVI), and development modifiers (see Research Disclosure Section XXI).

The photographic element can be coated on a variety of supports as described in Research Disclosure Section XVII and the references cited therein.

Photographic elements as described can be exposed to actinic radiation, typically in the visible region of the spectrum, to form a latent image as described in Research Disclosure Section XVIII, and then processed to form a visible dye image as described in Research Disclosure Section XIX. Processing to form a visible dye image includes the step of contacting the elements with a color developing agent to reduce developable silver halide and oxidize the color developing agent. Oxidized color developing agent in turn reacts with the coupler to yield dye. In this processing the coupling-off group as described is released.

Preferred color developing agents are p-phenylenediamines. Especially preferred are: 4-amino-N,N-diethylaniline hydrochloride; 4-amino-3-methyl-N,N-diethylaniline hydrochloride; 4-amino-3-methyl-N-ethyl-N-$\beta$-(methylsulfonamido)-ethylaniline sulfate hydrate; 4-amino-3-methyl-N-ethyl-N-$\beta$-(methylsulfonamido)-N,N-diethylaniline hydrochloride; 4-amino-N-ethyl-N-(2-methoxy-ethyl)-m-toluidine-di-p-toluene sulfonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the elements to render the unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The invention is further illustrated by the following examples, without being limited thereby. In the syntheses of representative compounds, Me designates a methyl group and t-Bu a tertiary butyl group.

SYNTHESIS EXAMPLE 1: Synthesis of Coupler 5 (Sample 5)

The synthesis is illustrated in the following reaction scheme:

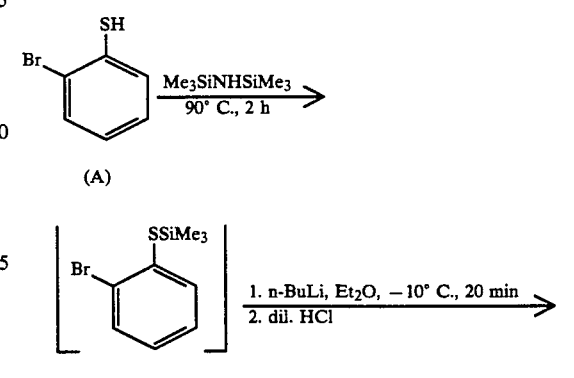

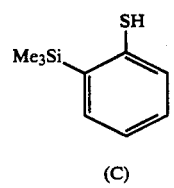

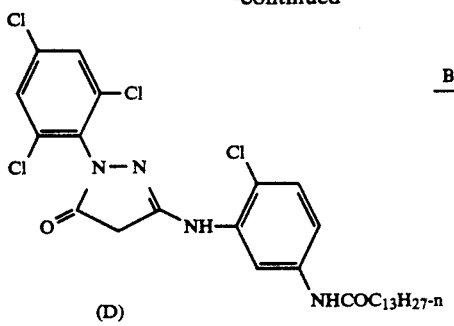

(D)

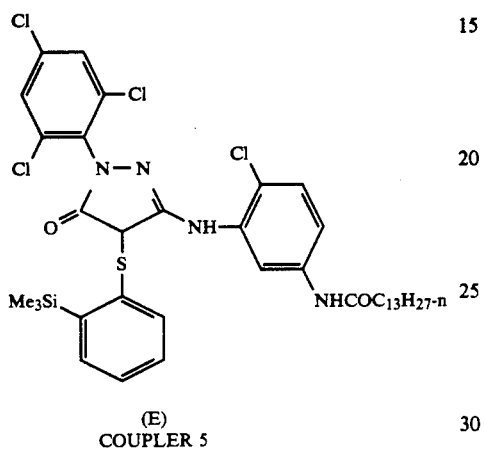

(E)
COUPLER 5

A thoroughly dried reaction vessel, cooled under a stream of argon, was charged with o-bromobenzenethiol (A) (6.34 g, 33.5 mmol), 1,1,1,3,3,3-hexamethyldisilazane (7 mL, 33.5 mmol) and imidazole (0.025 g to serve as a catalyst). The well-stirred mixture was heated to 90° C. and the course of the reaction was monitored by NMR (90 MHz) to completion. Excess hexamethylsilazane was removed under reduced pressure to yield o-bromo-S-(trimethylsilyl)benzenethiol (B) (94% yield) as the single clean product as indicated by H NMR analysis (300 MHz, CDCl$_3$).

Using a graduated, pressure-equalizing addition funnel, diethyl ether (30 mL) was added to the reaction vessel. The reaction mixture was thoroughly stirred and maintained at −10° C. by means of an ice-acetone bath as 13.8 mL (34.4 mmol) of a 2.5M solution of n-butyllithium in hexane was added dropwise over 3 minutes. After 20 minutes, the reaction was arrested by the addition of water (5 mL) followed by addition of dilute hydrochloric acid (10 mL of a 3.0M solution). The organic phase of the reaction mixture was separated and the aqueous phase was extracted with three 50 mL portions of diethyl ether. The combined extracts were then washed twice with 50 mL portions of saturated brine solution and dried over magnesium sulfate. Volatile solvents were removed using a rotary evaporator at 40° C. followed by drying of the product under vacuum. This yielded o-trimethylsilylphenol (C) as a pale yellow liquid (5.3 g, 87% yield based on o-bromobenzenethiol) as identified by $^1$H NMR (300 MHz, CDCl$_3$), consistent with the expected structure.

A 50 mL flask with magnetic stirring bar was charged with o-trimethylsilylthiophenol (2.27 g, 12 mmol) and N,N-dimethylformamide (DMF) (10 mL). To this well-stirred solution, maintained at 25° C., bromine (2.18 g, 13.6 mmol) dissolved in 10 mL DMF was added dropwise by addition funnel. The formation of the corresponding sulfenyl bromide was clean and instantaneous. The arylthiosulfenyl bromide thus generated was added dropwise to a well-stirred solution of the coupler (D) (6.96 g, 11.3 mmol) in 15 mL DMF maintained at room temperature (ca. 25° C.). The reaction mixture was stirred initially at room temperature for a period of 2 h, followed by gentle heating (45°–50° C.). The reaction was monitored to completion (1 h) by thin layer chromatography (TLC). The mixture was cooled and poured into crushed ice. The crude product was then filtered (6.7 g) and was further purified by recrystallization from acetonitrile (5.8 g, 58% yield) to give the coupler (E) (coupler 5) as a white solid.

HPLC: 93%, m.p. 240°–41° C.

| Elemental analysis for C$_{38}$H$_{48}$Cl$_4$O$_2$N$_4$SSi: | | | | | | | |
|---|---|---|---|---|---|---|---|
| calculated: | C: | 57.4 | H: | 6.09 | N: | 7.05 |
| found: | C: | 56.8 | H: | 6.00 | N: | 6.90 |

SYNTHESIS EXAMPLE 2: Synthesis of Coupler 7 (Sample 7)

The synthesis is illustrated in the following reaction scheme:

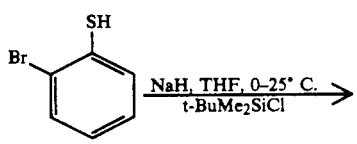

(A)

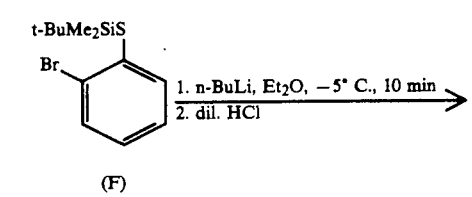

(F)

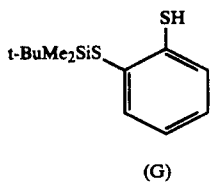

(G)

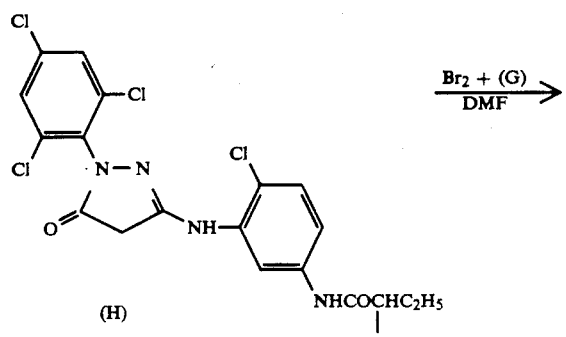

(H)

-continued

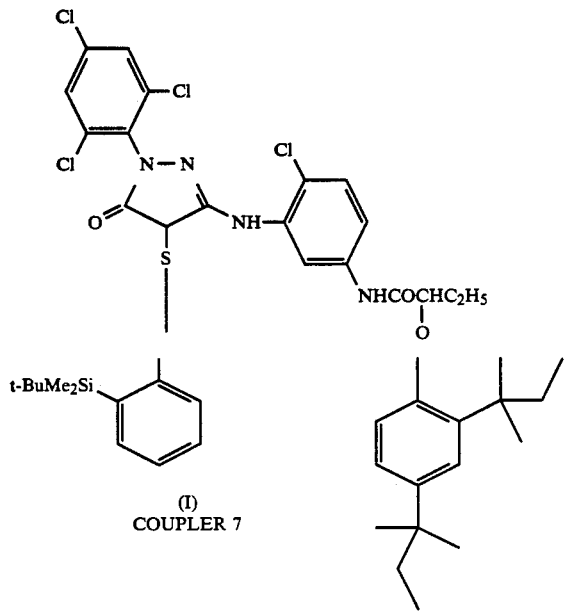

(I)
COUPLER 7

A dry 500 mL round bottom flask, equipped with a magnetic stirring bar, maintained under static argon atmosphere, was charged with sodium hydride (4.55 g, 112 mmol in mineral oil, 60% by weight) and dry THF (80 mL). To this well-stirred slurry, maintained at 0° C. (ice bath) was added o-bromothiophenol (A) (18.7g, 99 mmol). Reaction was rapid with vigorous hydrogen evolution. After 15 min, t-butyldimethylsilyl chloride (17.13 g, 114 mmol.) dissolved in 35 mL of THF was added dropwise over 15 min. The resulting mixture was stirred overnight, and the precipitated sodium chloride was filtered off. The volatile materials were then distilled off under atmospheric pressure to provide the crude product (17 g) as a pale yellow oil. The oil was further purified by vacuum distillation under argon, bp 99°–100° C., (0.4 mm) to yield o-bromo(S-tertbutyldimethylsilyl)benzenethiol (F) as a colorless liquid (14.4 g, 48% yield). HPLC: 96% pure. $^1$H NMR (300 MHz) was consistent with the structure.

To a well-stirred solution of (F) (10.6 g, 36 mmol) in 35 mL of anhydrous ether, maintained at −5° to −10° C., was added 15.7 mL of a 2.5M solution of n-butyllithium (15.7 mL, 39 mmol) in hexane. After a total reaction time of 11 min, the reaction was quenched by the addition of water (5 mL) by means of a hypodermic syringe. A 6N solution of hydrochloric acid (15 mL) was added, and the mixture extracted with ether. The combined extracts were washed with brine and dried over MgSO$_4$. Removal of solvents provided o-(tertbutyldimethylsilyl)benzenethiol (G) as a colorless liquid (8.0 g, yield), essentially pure (NMR). A portion (3.95 g) of this was further purified by vacuum distillation to afford 2.74 g (74% yield) as a colorless liquid, bp 102°–105° C. (1.5 mm).

A 35 mL flask was charged with (G) (2.66 g, 12 mmol) and DMF (8 mL). The mixture was thoroughly stirred and maintained at 25° C. Bromine (2.09 g, 13 mmol) dissolved in 5 mL of DMF was added to the mixture. The resulting sulfenyl bromide thus formed was added dropwise to a well-stirred slurry of the coupler (H) in 15 mL of DMF maintained at 25° C. under argon. During the addition the coupler (H) went into solution and the resulting mixture was stirred at room temperature (20° C.) for 12 hours until reaction completion as measured by TLC. The mixture was poured into crushed ice and filtered to provide the desired coupler (I) (coupler 5) (10.1 g, 100% yield) as a green solid. The product was further purified by recrystallization from hot acetonitrile to yield 7.9 g (79%) of the pure coupler (I) (coupler 7) having a melting point of 239° C. H NMR was consistent with the structure. HPLC=98%.

| Elemental analysis: | | | | | | | |
|---|---|---|---|---|---|---|---|
| calculated: | C: | 60.77 | H: | 6.30 | N: | 6.00 |
| found: | C: | 60.54 | H: | 6.11 | N: | 5.92 |

Other similar couplers can be prepared in the same manner but replacing the tert-butyldimethylsilyl group with a silyl group such as n-butyldimethyl, tripropyl, triethyl, tributyl, tripentyl, methoxydiethyl, ethyldimethyl, propyldimethyl, octyldimethyl, ethylmethylbutyl, etc.

EXAMPLES 1–7

Photographic elements were prepared by coating a gel-subbed polyethylene-coated paper support with a photosensitive layer containing a silver chloride emulsion at 0.172 g Ag/m$^2$, gelatin at 1.24 g/m$^2$, and each magenta image dye-forming coupler indicated in Table I at 0.426 mmol/m$^2$ dispersed in an equal weight of tricresyl phosphate. Each coupler dispersion also contained the following addenda (weight percent of coupler): A-1 (48%), A-2 (29%), A-3 (32%), A-4 (16%), and ethyl acetate (300%). The photosensitive layer was overcoated with a UV-absorbing layer containing 1.31 g/m$^2$ gelatin and a mixture of Tinuvin ® 328 at 732 g/m$^2$ and Tinuvin ® 326 at 129 g/m$^2$ (Tinuvin ® is a trademark of Ciba-Geigy Corp.). This was overcoated with a protective layer containing 1.35 g/m$^2$ gelatin and bis(vinylsulfonylmethyl)ether hardener at 2 wt % based on total gelatin. The format is shown below:

| OC | Gelatin (1.35 g/m$^2$) |
|---|---|
| | bis(vinylsulfonylmethyl) ether |
| | hardener (2 wt % based on total gelatin) |
| OC | Gelatin (1.31 g/m$^2$) |
| | Tinuvin ® mixture |
| PHOTO- | Gelatin (1.24 g/m$^2$) |
| SENSITIVE | AgCl emulsion (0.172 g Ag/m$^2$) |
| LAYER | magenta image dye-forming coupler from from Table I (0.426 mmol/m$^2$), dispersed in equal weight of tricresyl phosphate Addenda A-1 to A-4 |
| FILMBASE | gel-subbed polyethylene-coated paper |

Addendum A-1: (Compound No. I-1 in U.S. Pat. No. 4,217,410)

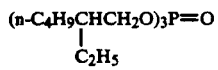

Addendum A-2: (Compound No. 21 in U.S. Pat. No. 4,360,589)

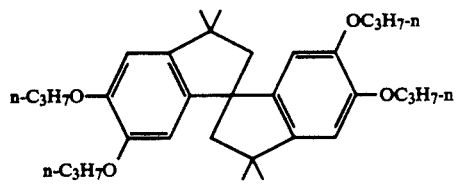

Addendum A-3: (Compound No. II-10 in EP 81,768)

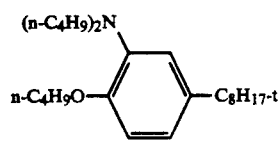

Addendum A-4: (Compound No. 104 in EP 69,070)

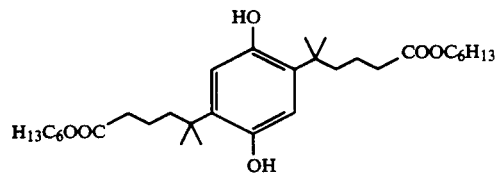

Samples of each element were exposed through a graduated-density test object, processed at 35° C. for 45 sec each in the color developer and in the bleach-fix bath, then washed and dried. The compositions of the processing baths were as follows:

| Color developer (pH 10.15) | |
|---|---|
| Triethanolamine | 12.41 g |
| Lithium polystyrenesulfonate (30% soln.) | 0.30 g |
| N,N-diethylhydroxylamine (85% soln.) | 5.40 g |
| 4-Amino-3-methyl-N-ethyl-N-(methanesulfon-amido)-ethylaniline sulfate hydrate | 5.00 g |
| Stilbene whitening agent | 2.30 g |
| 1-Hydroxyethylene-1,1-diphosphonic acid (60% soln.) | 1.16 g |
| Lithium sulfate | 2.70 g |
| Potassium carbonate (anhydrous) | 21.16 g |
| Potassium bicarbonate | 2.79 g |
| Potassium chloride | 1.60 g |
| Potassium bromide | 0.028 g |
| Potassium hydroxide (45% soln.) | 0.816 ml |
| Water to make | 1.0 L |
| Bleach-Fix bath (pH 6.8) | |
| Ammonium thiosulfate | 104.0 g |
| Sodium hydrogen sulfite | 13.0 g |
| Ferric ammonium ethylenediamine tetraacetic acid (EDTA) | 65.6 g |
| EDTA | 6.56 g |
| Ammonium hydroxide | 27.9 g |
| Water to make | 1.0 L |

The densitometric contrast (gamma) to green light of each resulting dye image was determined, and replicate processed strips were subjected to the following accelerated keeping tests:

I) 12-week fading under a 5.4 Klux xenon exposure, using a Wratten 2B filter to remove the UV component: percent image fading (Fade) and background printout (dDmin) were read with green light.

II) 2-week keeping in a 77° C./15% relative humidity oven: increases in background density (dDmin) to green light (pinking) and to blue light (yellowing) were measured.

The results are presented in Table I.

TABLE I

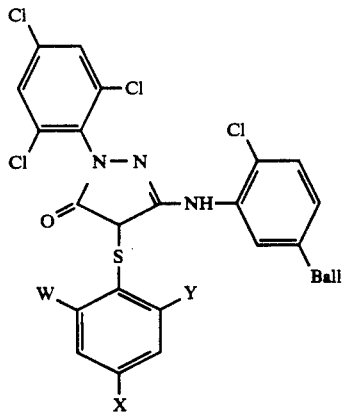

| | | | | | | Xenon Light | | Oven Dmin | |
| Sample* | Ball | W | X | Y | Gamma | % Fade | dDmin | Green | Blue |
|---|---|---|---|---|---|---|---|---|---|
| 1. Comp. | B-1 | Me | Me | Me | 2.94 | −59 | 0.09 | 0.17 | 0.29 |
| 2. Comp. | B-1 | Me | Cl | Me | 2.73 | −32 | 0.09 | 0.16 | 0.27 |
| 3. Comp. | B-1 | Me | H | Me | 2.32 | −59 | 0.10 | 0.13 | 0.22 |
| 4. Comp. | B-1 | H | H | t-Bu | 2.79 | −29 | 0.10 | 0.05 | 0.10 |
| 5. Invn. | B-1 | H | H | Me$_3$Si | 2.82 | −26 | 0.08 | 0.05 | 0.10 |
| 6. Invn. | B-2 | H | H | Me$_3$Si | 3.01 | −24 | 0.08 | 0.06 | 0.11 |

TABLE I-continued

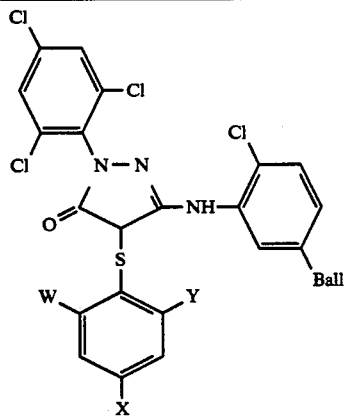

| Sample* | Ball | W | X | Y | Gamma | Xenon Light % Fade | dDmin | Oven Dmin Green | Blue |
|---|---|---|---|---|---|---|---|---|---|
| 7. Invn. | B-2 | H | H | t-BuMe$_2$Si | 3.07 | −24 | 0.08 | 0.05 | 0.10 |

*Invn. = samples of the invention; comp. = comparisons. Methyl and tertiary butyl groups are designated as Me and t-Bu, respectively.
Ball
B-1 —NHCOC$_{13}$H$_{27}$-n
B-2

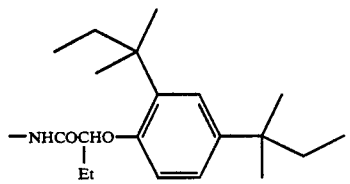

It can be seen from the data of Table I that the silyl-substituted couplers of the invention generally showed greater activity (gamma) than their non-silyl comparisons, and gave less background discoloration on exposure to heat and light. In addition, Samples 5-7 according to the invention provided dyes which were more stable to light fade than the closely related comparison samples.

It is to be understood that the foregoing detailed description and specific examples, while indicating preferred embodiments of the present invention, are given by way of illustration and not limitation. Many changes and modifications within the scope of the present invention may be made without departing from the spirit thereof, and the invention includes all such modifications.

What is claimed is:

1. A photographic element comprising a support and a silver halide emulsion layer having associated therewith a coupler having a coupling-off group which comprises a carbocyclic or heterocyclic ring which bears a silyl substituent having a silicon atom directly bonded to at least one of its ring carbon atoms and is attached via another of its ring atoms either directly or though a linking group or atom to the coupling position of said coupler, wherein said silyl substituent bears three groups which are independently aromatic groups, heterocyclic groups, aliphatic groups or additional silyl groups bonded through a linking atom to the silicon atom in said silyl substituent.

2. A photographic element as claimed in claim 1 wherein said coupler is represented by the formula:

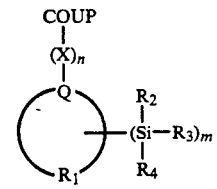

wherein
COUP is a coupler moiety;
m is 1, 2 or 3;
X is O, S, or a linking group;
n is 0 or 1;
Q is a carbon atom or nitrogen atom, with the proviso that when Q is carbon, n is 1 and X is O, S or amino, and when Q is nitrogen, n is 0 or 1 and X is —OC(R)$_2$—;
R is hydrogen, C$_{1-30}$ alkyl or C$_{6-30}$ aryl;
R$_1$ represents the atoms necessary to complete an unsubstituted or substituted carbocyclic or heterocyclic ring; and
R$_2$, R$_3$ and R$_4$ individually are unsubstituted or substituted groups that are hydrolytically stable and compatible with COUP.

3. A photographic element as claimed in claim 2, wherein R$_2$, R$_3$ and R$_4$ individually are unsubstituted or substituted C$_{1-30}$ alkyl, C$_{2-30}$ alkenyl, C$_{6-30}$ cycloalkyl, C$_{6-30}$ aryl, heterocyclic, silyloxy, C$_{1-30}$ alkoxy or C$_{6-30}$ aryloxy groups.

4. A photographic element as claimed in claim 3, wherein R$_2$, R$_3$ and R$_4$ individually are unsubstituted or substituted C$_{1-30}$ alkyl groups, C$_{2-30}$ alkenyl groups, or silyloxy groups.

5. A photographic element as claimed in claim 2, wherein R₁ represents the carbon, nitrogen and/or oxygen atoms necessary to complete a 5- or 6-member carbocyclic or heterocyclic ring.

6. A photographic element as claimed in claim 5, wherein R₁ and Q jointly form a benzene ring.

7. A photographic element as claimed in claim 1, wherein said coupling-off group is an o-trialkylsilylarylthio coupling-off group.

8. A photographic element as claimed in claim 1 wherein said coupler is a cyan, magenta or yellow image dye-forming coupler.

9. A photographic element as claimed in claim 1, wherein said coupler is selected from the group consisting of:

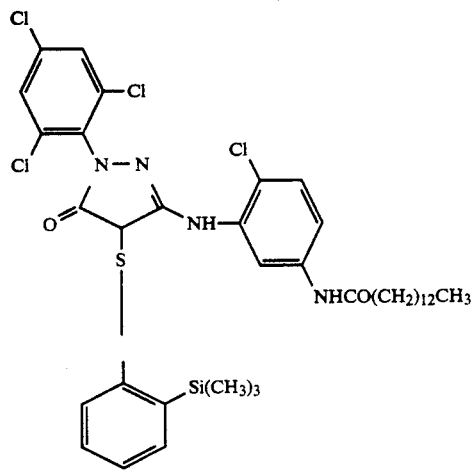

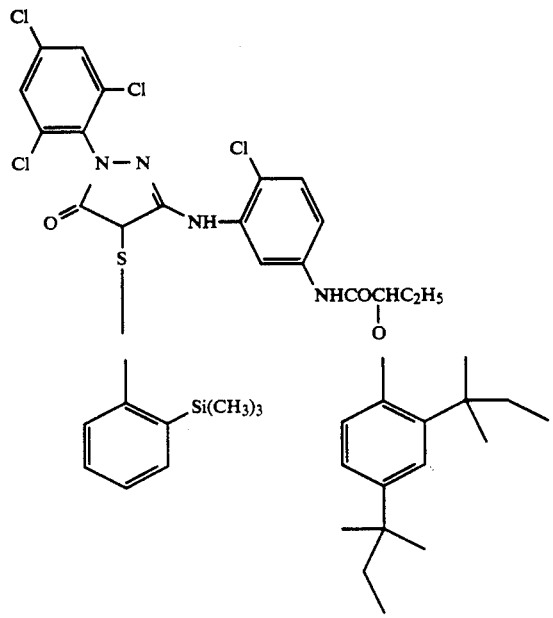

and

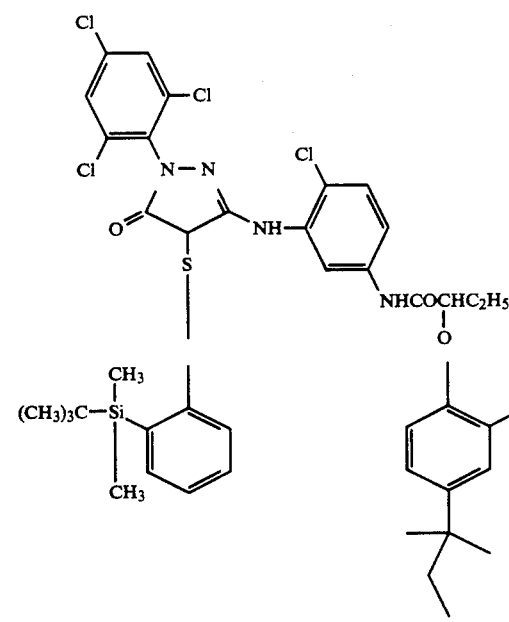

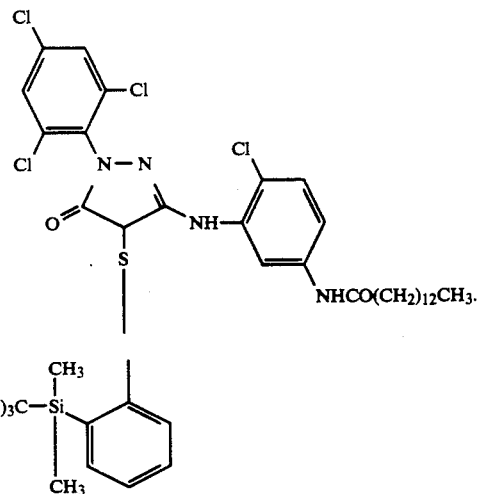

10. A multicolor photographic element comprising a support bearing a cyan dye image-forming unit comprising at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler, wherein at least one of said image forming units comprises a coupler having a coupling-off group which comprises a carbocyclic or heterocyclic ring which bears a silyl substituent having a silicon atom directly bonded to at least one of its ring carbon atoms and is attached via another of its ring atoms either directly or through a linking group or atom to the coupling position of said coupler, wherein said silyl substituent bears three groups which are independently aromatic groups, heterocyclic groups, aliphatic groups or additional silyl groups bonded through a linking atom to the silicon atom in said silyl substituent.

11. A process for developing an image in a photographic element comprising a support and a silver halide emulsion containing an imagewise distribution of developable silver halide grains, said process comprising the step of developing said element with a silver halide color developing agent in the presence of a photographic coupler having a coupling-off group which comprises a carbocyclic or heterocyclic ring which bears a silyl substituent having a silicon atom directly bonded to at least one of its ring carbon atoms and is attached via another of its ring atoms either directly or through a linking group or atom to the coupling position of said coupler, wherein said silyl substituent bears three groups which are independently aromatic groups, heterocyclic groups, aliphatic groups or additional silyl groups bonded through a linking atom to the silicon atom in said silyl substituent.

12. A photographic silver halide emulsion comprising a photographic coupler having a coupling-off group which comprises a carbocyclic or heterocyclic ring which bears a silyl substituent having a silicon atom directly bonded to at least one of its ring carbon atoms and is attached via another of its ring atoms either directly or through a linking group or atom to the coupling position of said coupler, wherein said silyl substituent bears three groups which are independently aromatic groups, heterocyclic groups, aliphatic groups or additional silyl groups bonded through a linking atom to the silicon atom in said silyl substituent.

13. A photographic silver halide emulsion as claimed in claim 12, wherein said coupler is represented by the formula:

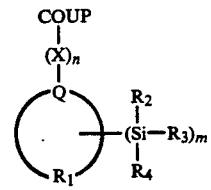

wherein
COUP is a coupler moiety;
m is 1, 2 or 3;
X is O, S, or a linking group;
n is 0 or 1;
Q is a carbon atom or nitrogen atom, with the proviso that when Q is carbon, n is 1 and X is O, S or amino, and when Q is nitrogen, n is 0 or 1 and X is $-OC(R)_2-$;
R is hydrogen, $C_{1-30}$ alkyl or $C_{6-30}$ aryl;
$R_1$ represents the atoms necessary to complete an unsubstituted or substituted carbocyclic or heterocyclic ring; and
$R_2$, $R_3$ and $R_4$ individually are unsubstituted or substituted groups that are hydrolytically stable and compatible with COUP.

14. A photographic silver halide emulsion as claimed in claim 13, wherein $R_1$ represents the carbon, nitrogen and/or oxygen atoms necessary to complete a 5- or 6-member carbocyclic or heterocyclic ring.

* * * * *